United States Patent
Milo et al.

[11] Patent Number: 5,816,923
[45] Date of Patent: Oct. 6, 1998

[54] FLEXIBLE COMPOSITE DRIVE SHAFT FOR TRANSMITTING TORQUE

[75] Inventors: Charles Milo, Union City; William Earl Webler, Newark; Fred Henrik Co, Santa Clara, all of Calif.

[73] Assignee: Devices for Vascular Intervention, Inc., Redwood City, Calif.

[21] Appl. No.: 606,678

[22] Filed: Feb. 26, 1996

Related U.S. Application Data

[63] Continuation of Ser. No. 165,058, Dec. 9, 1993, abandoned.

[51] Int. Cl.$^6$ ........................................ F16C 1/00
[52] U.S. Cl. .......................... 464/58; 464/174; 464/902
[58] Field of Search ................... 464/902, 58, 57, 464/173, 174; 74/502.5

[56] References Cited

U.S. PATENT DOCUMENTS

| | | | |
|---|---|---|---|
| Re. 33,569 | 4/1991 | Gifford, III et al. | 128/752 |
| 3,043,120 | 7/1962 | Waldron | 64/2 |
| 3,581,523 | 6/1971 | Bartholomew | 64/2 |
| 3,726,133 | 4/1973 | Morgan | 73/118 |
| 4,601,283 | 7/1986 | Chikama | 128/4 |
| 4,655,629 | 4/1987 | Flaherty | 403/291 |
| 4,771,774 | 9/1988 | Simpson | 128/305 |
| 4,781,186 | 11/1988 | Simpson | 128/305 |
| 4,794,931 | 1/1989 | Yock | 128/660 |
| 4,979,951 | 12/1990 | Simpson | 606/159 |
| 5,000,185 | 3/1991 | Yock . | |
| 5,007,917 | 4/1991 | Evans | 606/170 |
| 5,041,089 | 8/1991 | Mueller | 604/96 |
| 5,071,425 | 12/1991 | Gifford, III et al. | 604/97 |
| 5,072,759 | 12/1991 | Moore | 138/153 |
| 5,078,722 | 1/1992 | Stevens | 606/159 |
| 5,084,010 | 1/1992 | Plaia | 604/22 |
| 5,085,662 | 2/1992 | Willard | 606/159 |
| 5,087,265 | 2/1992 | Summers | 606/159 |
| 5,092,873 | 3/1992 | Simpson et al. | 606/7 |
| 5,100,424 | 3/1992 | Jang | 606/159 |
| 5,101,682 | 4/1992 | Radisch, Jr. et al. | 74/502.6 |
| 5,102,415 | 4/1992 | Guenther | 606/159 |
| 5,108,411 | 4/1992 | McKenzie | 606/159 |
| 5,135,531 | 8/1992 | Shiber | 606/159 |
| 5,156,610 | 10/1992 | Reger | 606/159 |
| 5,158,564 | 10/1992 | Schnepp-Pesch | 606/159 |
| 5,165,421 | 11/1992 | Fleischhacker et al. | 128/772 |
| 5,226,909 | 7/1993 | Evans | 606/159 |
| 5,239,890 | 8/1993 | Sosnoski et al. | 74/501.5 R |
| 5,250,059 | 10/1993 | Andreas | 606/159 |
| 5,360,432 | 11/1994 | Shturman | 606/159 |
| 5,514,115 | 5/1996 | Frantzen et al. | 604/281 |

*Primary Examiner*—Donald P. Walsh
*Assistant Examiner*—William A. Rivera
*Attorney, Agent, or Firm*—Peninsula IP Group; Douglas A. Chaikin, Esq.

[57] ABSTRACT

A flexible composite drive shaft used with a flexible vascular atherectomy catheter for connecting a proximal rotating drive member and a distal rotatable working member. The flexible composite drive shaft includes a core of specially selected highly elastic shape memory alloy surrounded by a flexible torsional reinforcing helical wound member and a covering of a smooth polymeric material penetrating the interstices between the wound member and the outer surface of the core. The material of the core, the relative winding direction of the reinforcing member and the direction of angular offset between the reinforcing member and the core are selected to optimize the consistency of the rotational characteristics of the drive shaft in use. The cooperation between the shape memory elastic core, the helical reinforcing member and the interpenetrating polymer provides a composite drive shaft which has improved resistance to kinking and binding failure while traversing tight radii, narrow blood vessel pathways during axial translation and high speed rotational operation.

35 Claims, 4 Drawing Sheets

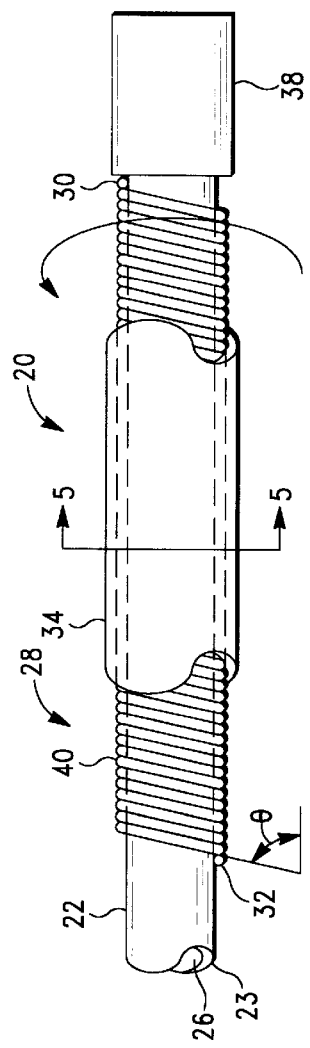
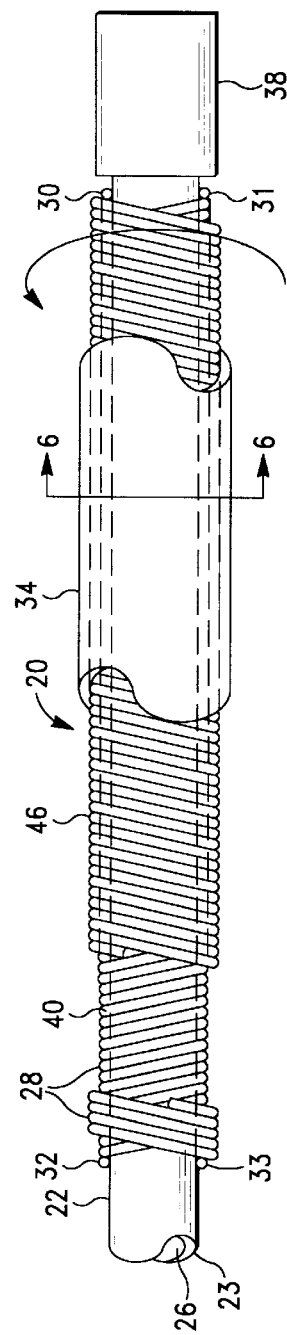
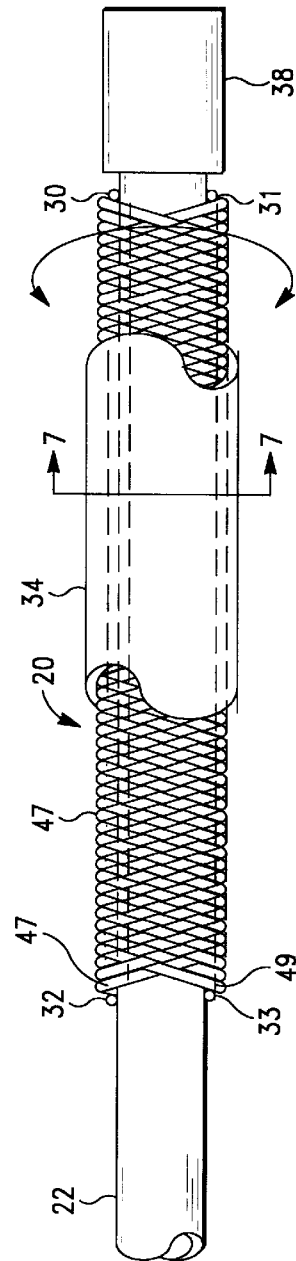
FIG.-2
FIG.-3
FIG.-4

FLEXIBLE COMPOSITE DRIVE SHAFT FOR TRANSMITTING TORQUE

This Application is a file wrapper continuation of U.S. application Ser. No. 08/165,058, filed Dec. 9, 1993, now abandoned.

BACKGROUND OF THE INVENTION

1. Field of the Invention

The present invention relates generally to internal drive shafts used in conjunction with vascular catheters for rotating a work performing element. More particularly, the present invention relates to a flexible composite drive shaft.

2. Previous Art

Atherectomy procedures using various catheter instruments for imaging and surgically removing portions of stenoses in the human vascular system are well known. Examples of surgical procedures are provided in U.S. Pat. No. Re 33,569 to Gifford et al., U.S. Pat. No. 5,071,425 to Gifford, and U.S. Pat. No. 5,092,873 to Simpson et al. These patents generally teach a housing having a window connected to the distal end of a catheter, a cutter enclosed within the housing and exposed through the window for removing a portion of the stenosis, a lumen within the catheter for passage of the cutter, and a drive shaft for connecting the cutter to a proximal drive coupling means.

Stenotic tissue takes a number of different forms. Some stenoses are soft and flexible. Soft stenoses typically require a catheter to have a drive shaft with an acceptable degree of axial stiffness for accurately moving a work performing element with very sharp cutting edges to precisely cut small, flexible flaps of tissue. Other stenoses take the form of hard, calcified deposits. Hard, calcified deposits typically require a catheter having a drive shaft with acceptable axial stiffness to apply considerable axial force with a sharp, durable cutter against the deposits.

Vascular catheters may have rotating ultrasonic imaging devices attached at the distal end for imaging a region of a blood vessel having an atheroma before and after an interventional treatment. Such catheters frequently utilize a flexible drive cable or shaft in order to transmit a rotational drive force from a driving device such as a motor located at the proximal end of the catheter to a work performing element located at the distal end.

Ultrasonic imaging is used to improve identification of the nature, extent and location of the stenoses during surgery. Ultrasonic imaging is also used to determine the method of treatment and the resultant effect. The use of such imaging is exemplified in U.S. Pat. application Ser. No. 08/051,521 by Milo, et al. herein incorporated by reference. As taught in this patent application, ultrasonic energy is generated by a transducer located at the distal end of, or within a vascular catheter. The transducer is manipulated rotationally and axially to a desired position by a drive shaft means to sweep a ultrasonic signal in a desired pattern.

Ultrasonic energy reflected from the different layers of the blood vessel, including any stenosis or occlusion present, is processed by a display processor and the result used to display an image or profile of the interior of the vessel. The display of the image is typically presented on a monitor connected to the display processor. The resulting image is typically a picture showing a cross sectional representation of the vessel looking outward from the center of the vessel. The picture may be a cross section showing the radial topography of the vessel perpendicular to the axis, or a cross section showing a longitudinal topography in the axial direction of the vessel.

The position of the transducer in the blood vessel is critical to the accuracy of the image as the representation of the interior of the vessel. The rotational and axial transducer position in the blood vessel is typically inferred from the rotational and axial position of encoders mounted on the proximal end of the drive shaft. Any variation in position of the transducer at the distal end of the drive shaft with respect to the proximal end will result in error in the image as a representation of the shape of the actual blood vessel. A rotationally and axially stiff drive shaft is needed to give an accurate image representation.

It is also important that the drive shaft provide high torsional strength and stiffness to minimize variation in the rotational velocity of the imaging element on the distal end of the catheter. Fluctuations of rotational velocity of the imaging element cause distortion in the resulting image display.

The rotational motion of the work performing element at the distal end of the catheter is provided by the torsional force, i.e., torque transmitted from a motor drive unit (MDU) through the drive shaft. The drive shaft must have sufficient torsional stiffness in order to deliver adequate rotational force to the work performing element along the relatively long path through the catheter connecting the drive means to the work performing element.

It is particularly important that the drive shaft provide a high torsional stiffness such that the distal end of the drive shaft and the proximal end of the drive shaft turn nearly together without appreciable rotational lag. Rotational lag is a difference between the angular displacement of one end of the drive shaft with respect to the other. The rotational lag between the distal and proximal ends of the drive shaft under load is commonly referred to as "wind up" which it experiences due to the high length to diameter aspect ratio.

In addition to rotation, it is frequently desirable to be able to translate the work performing element in an axial direction within the catheter, preferably simply by pushing or pulling on the proximal end of the drive shaft.

It is additionally important that the drive shaft be capable of a high degree of lateral bending without "kinking" or fracturing. This attribute is required to negotiate the tortuous passages of the vascular system without causing the drive shaft to bind or seize up in the catheter, or possibly shatter due to material fatigue, potentially causing damage to the patient.

The attributes of lateral flexibility and torsional strength are simultaneously required while the drive shaft is rotating, frequently at high rpm while also being translated in an axial direction.

It is well known in the art to use drive cables consisting of solid wires, wound springs or braided cables. Typically, compromises must be made to achieve acceptable degrees of torsional stiffness, bending flexibility and axial stiffness to minimize excessive windup, easily negotiate tight curves and accurately position the working element in the catheter. For some applications, e.g. ultrasonic imaging, the accuracy of angular position is important for providing an accurate representation of the layers of the vessel walls being studied. Excessive windup and rotational velocity fluctuation is particularly important to minimize in these cases.

The drive shaft used in atherectomy procedures as described above includes an elongated member, usually a narrow diameter cylindrical member. This elongated member rotationally connects a rotating means, such as a mechanical coupler located at the proximal end of the catheter, with the work performing element located at the distal end of the catheter.

Various means to provide flexible drive shaft structures have been employed. U.S. Pat. No. 5,108,411, discloses a vascular catheter having a flexible drive shaft extending through a central lumen. The shaft is formed of essentially two distinct proximal and distal sections having different construction and different bending and torsional flexibility. The embodiment is disclosed as having a proximal section of solid 304V stainless steel and a distal section of 304V stainless steel helical wound springs. These two distinct sections have different torsional and flexural characteristics. An elastomeric coating over the two sections is provided to reduce friction and enhance rotation of the drive shaft within the catheter lumen.

Atherectomy drive shafts of solid wire are also known. An example is disclosed in Willard, U.S. Pat. No. 5,085,662. This discloses a drive shaft having a core of solid wire of 304 stainless steel to provide axial stiffness, surrounded by a set of smaller wires of lower ultimate strength and higher flexibility. Another approach is to provide a central core wire having a taper at the distal end encapsulated by a 12 to 16 wire braid of 0.002 to 0.003 in. stainless steel wire. These braids are composed of multiple strands or filaments of finer wire. These structures have bending characteristics which are primarily limited by the properties of the central core wire materials selected, i.e. stainless steel. There is no disclosure of cooperation between the polymeric coating material, the helical wound members and the central core member.

It is therefore desirable to provide improved drive shafts for vascular catheters having rotationally driven work performing elements at their distal end. Particularly, it is desirable to provide drive shafts which are sufficiently flexible to negotiate the tortuous passages through which catheters must pass, drive shafts with sufficient torsional stiffness to minimize rotational wind up, and sufficient flexural stiffness to avoid seizing and binding of the drive shaft in the catheter, and sufficient axial stiffness to provide accurate axial positioning. It is further desirable to provide drive shafts which are capable of negotiating the tight bending radii and narrow curvature within the vascular system while operating at high rotational speed without suffering from the effects of premature failure due to material fatigue. It is additionally desirable to provide drive shafts having very narrow diameters in order to allow catheters to be constructed which can enter very small diameter blood vessels.

What is needed is drive shaft structures for vascular catheters which allows freedom in providing drive shafts having torque transmission characteristics which can be optimized for different requirements. It is also desirable to provide drive shaft structures for vascular catheters having axial force transmission characteristics which can additionally be optimized for different requirements.

There is also a need for drive shaft structures for vascular catheters having high tolerance to tight bending requirements. It is also desirable to provide drive shaft structures for vascular catheters having low failure probability due to material fatigue at high rotational speeds.

There is also a need for flexible drive shafts which minimize wind-up while retaining acceptable rotational stiffness and lateral flexibility.

SUMMARY OF THE INVENTION

In general, it is an object in accordance with this invention, to provide a flexible composite drive shaft having sufficient rotational stiffness to transmit a rotational drive force from a driving device such as a motor located at the proximal end of the catheter to a work performing element located at the distal end.

In addition, it is an object in accordance with this invention to provide a flexible composite drive shaft having suitable axial stiffness to translate and position the work performing element accurately in an axial direction within the catheter.

In addition, it is an object in accordance with this invention to provide a composite drive shaft having suitable rotational stiffness and consistent in rotational velocity of the work performing and/or imaging element.

In addition, it is an object in accordance with this invention to provide that the composite drive shaft be capable of a high degree of lateral bending without failure.

In accordance with the above objects and those that will be mentioned and will become apparent below, the composite drive shaft adapted for use with a biological catheter in accordance with this invention, comprises:

an elongated core made from shape memory alloy, the core defining a cylindrical substrate having an outer surface, the core extending from the proximal end of the drive shaft through at least a substantial portion of the drive shaft, and a reinforcing member for reinforcing the torsional strength of the composite drive shaft, the reinforcing member surrounding the core having a first end attached to one end of the core, the reinforcing member having the other end attached to the opposite end of the core, whereby the combination of the core shape memory alloy which supports the reinforcing member provides improved torsional stiffness and improved axial stiffness to the drive shaft while retaining high lateral bending flexibility around the tortuous paths of the vascular system.

The improved axial stiffness of the composite drive shaft over that of conventional helical spring members, is provided by the shape memory alloy core. The improved rotational stiffness of the composite drive shaft over that of conventional helical spring members is provided by the combination of the support of the shape memory alloy core and the spring member. The high degree of lateral flexibility of the composite drive shaft is provided by the highly elastic nature of the shape memory alloy in combination with the reinforcing spring member.

A preferred embodiment of the composite drive shaft has a tubular shape memory alloy core surrounded by a reinforcing spring member which constitutes the first ⅔ of the drive shaft from the proximal end. The balance of the composite drive shaft is a conventional helical wound member connecting to the work performing element.

The attachment of the reinforcing member to the core may be made at one point at each end location. The attachment may alternately be made in multiple points at each end location, a sector of a circular region, or in some other suitable shape at each end location.

In a preferred embodiment of this invention, the core and the surrounding reinforcing member are coated with a polymeric coating which impregnates the interstices between the reinforcing member and the core.

In a preferred embodiment, the composite drive shaft is made from a shape memory alloy which is selected from one of the group of a first alloy constituting essentially nickel-titanium, a second alloy constituting essentially copper-zinc-aluminum and a third alloy constituting essentially copper-aluminum-nickel.

In an additional preferred embodiment the reinforcing member is a helical wound member wrapped around the outer surface of the core, the helical wound member including at least one filamentary element.

In a preferred embodiment of the composite drive shaft, the polymeric coating and impregnation within the interstices between the core and the reinforcing member acts to distribute forces such that the torsional stiffness of the composite is synergistically enhanced without significantly reducing the lateral flexibility. The combination of the three elements results in a composite drive shaft that exhibits the increased torsional stiffness characteristic of the material of the reinforcing member and the axial stiffness characteristics of the material of the core. The shape of the reinforcing member combined with the highly elastic nature of the shape memory alloy core material results in a composite drive shaft that has a very flexible lateral bending characteristic.

An additional preferred embodiment according to this invention has a helical wound member provided with a set of multiple strands or filamentary elements wound simultaneously. The strands are wound to be in contact with the core. The core acts as a rigid foundation or substrate for the strands which results in torsional forces being supported by the material of the strands.

The reinforcing member of one embodiment in accordance with this invention is a double wound member comprising a first helical wound member and an oppositely wound second helical member. The first member is comprised of one or more filamentary elements adjacent to the outer surface of the core and having a first winding direction and the second helical wound member is comprised of one or more filamentary elements defining a second winding direction.

In an additional embodiment of this invention, the second helical wound member is disposed outside the first helical wound member. The winding of the second member is such that the second member is in contact with the first member. The rotation of the composite drive shaft in use is such that the outside diameter of the first helical wound member tends to expand and the second member outside diameter tends to decrease. The result is an increase in the torsional stiffness characteristic of the composite drive shaft above that of the core material alone.

The first helical wound member in another embodiment in accordance with this invention is intertwined and braided with the second helical wound member over the length of the core of the composite drive shaft. The braided structure provides torsional stiffness characteristics essentially equal in both directions of rotation of the composite drive shaft.

In another embodiment, the end of the core and the end of the reinforcing member at the second attachment point are angularly displaced relative to the first attachment point. The end of the core and the end of the reinforcing member are also angularly displaced oppositely to each other. The angular displacements of the core end and the reinforcing member end are held in place before forming the second attachment point. The core and reinforcing member are then released and allowed to come to an equilibrium rotational position.

The core relaxes from a maximum rotational strain in one direction toward zero strain. The spring member absorbs rotational strain until the combination reaches equilibrium. The core and the reinforcing member are thereby preloaded with opposed torsional strain. The direction of preloaded torsional strain in the core is selected to be in opposition to the direction of torsional strain added during use. The torsional strain in use thereby subtracts from the preloaded torsional stain in the core.

The opposed direction of preloaded torsional strain and the in use torsional strain thereby cause an increase in the allowable maximum total angular displacement of the core, in use, before reaching an absolute maximum angular strain in the core.

The preloading direction for the above embodiment is selected to be in an angular direction to bring the reinforcing member in contact with the core after the second attachment is made and the core is released. The reinforcing member is thereby caused to tighten down on the core. This results in a higher torsional stiffness characteristic for the composite drive shaft.

In another embodiment, the displacement of the end of the core and the end of the reinforcing member and the attachment are first positioned as described above.

The opposed direction of preloaded torsional strain and the in use torsional strain thereby cause an increase in the allowable maximum total angular displacement of the core, in use, before reaching an absolute maximum angular stress in the core.

In addition, the direction of preloading is in such a direction as to bring the reinforcing member away from contact with the core during use. The composite drive shaft of this embodiment will have an increased resistance to failure due to additional angular displacement between proximal and distal ends during use.

In another embodiment, the reinforcing member includes a double wound spring having an inner winding and an outer winding. The two windings are wound in opposite directions. The inner winding is wound to be in contact with the core and the outer winding is wound to be in contact with the inner winding. The windings are impregnated with a polymeric coating of polyethylene. The winding direction and preloading in this embodiment is such that the torsional strain in the core is nearly equal to the beginning of a first superelastic region of the core in a first direction of angular displacement, whereby a torsional load placed in opposition to the preloaded strain will cause the core to traverse the full span of elastic strain from the first superelastic region to a second superelastic region in a second rotational direction opposite to the first direction of angular displacement. This structure provides a significant increase in the amount of rotation with a high torsional stiffness coefficient.

Suitable treatment of the polymeric coating such as heating, causes it to penetrate the interstices between the reinforcing member and the core. This penetration makes contact of the polymeric material with the reinforcing member and the outer surface of the core; whereby coupling forces between the reinforcing member and the core are more uniformly distributed. The coating filled interstices of this embodiment combined with the high elasticity of the selected core material causes an increase in the amount of angular displacement between the proximal and distal ends of the drive shaft before failure and an increase in the torsional stiffness coefficient of the composite drive shaft.

It is an advantage of this invention to provide an atherectomy apparatus having a flexible composite drive shaft having sufficient rotational stiffness to accurately transmit rotational drive force from the proximal end of the catheter to a work performing element located at the distal end.

It is an additional advantage of this invention to provide an apparatus capable of accurately translating and positioning a work performing element within a catheter.

It is an additional advantage of this invention to provide an atherectomy apparatus capable of operating with improved consistency in angular velocity of a work performing and/or imaging element.

It is an additional advantage of this invention to provide a composite drive shaft having improved resistance to failure due to material fatigue at high rotational speed around tortuous bends.

BRIEF DESCRIPTION OF THE DRAWING

For a further understanding of the objects and advantages of the present invention, reference should be had to the following detailed description, taken in conjunction with the accompanying drawing, in which like parts are given like reference numerals and wherein:

FIG. 2 is a schematic partial side view of a composite drive shaft having a single spring member in accordance with this invention.

FIG. 3 is a schematic partial side view of a second embodiment having a double wound spring member in accordance with this invention.

FIG. 4 is a schematic partial side view of a third embodiment having a braided spring member in accordance with this invention.

DETAILED DESCRIPTION OF THE INVENTION

Figure 1:
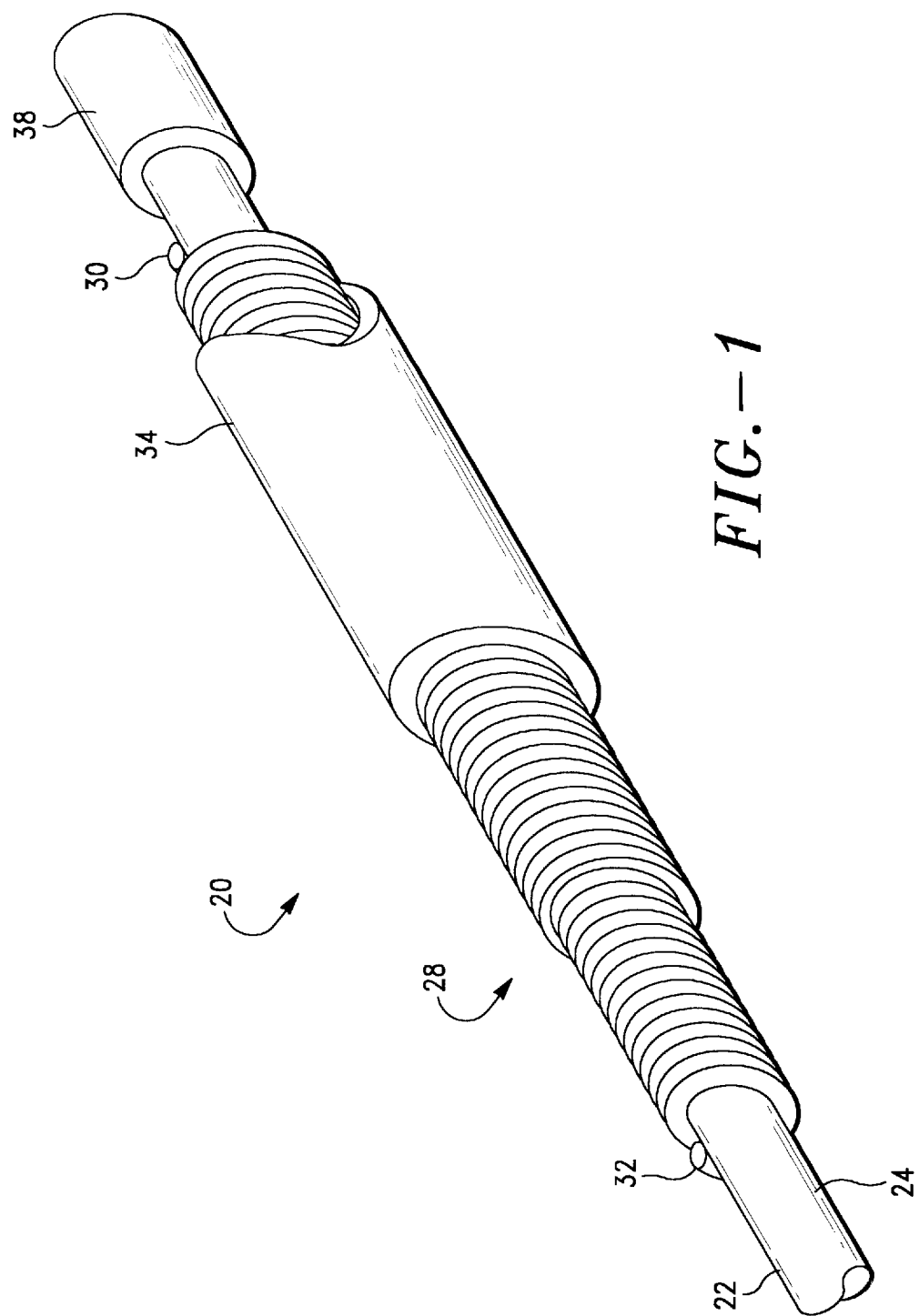
FIG. 1 is a schematic partial perspective view of a composite drive shaft in accordance with this invention.

The invention will now be described with reference to FIGS. 1 and 2 wherein the composite drive shaft in accordance with this invention is shown generally by the numeral 20. The composite drive shaft 20 includes an elastic core 22, having an outer surface 24, a reinforcing member 28 surrounding the core 22, a polymeric coating 34 surrounding the member 28 and a drive coupling means 38 connected to the proximal end of the core 22. The distal end of the core 22 is connected to a work performing element (not shown). The material for core 22 is selected from the group of shape memory alloys. The preferred shape memory alloy is one of an alloy consisting essentially of nickel-titanium, or an alloy consisting essentially of copper-aluminum-nickel or an alloy consisting essentially of copper-zinc-aluminum. A preferred shape memory alloy is nickel-titanium. Shape memory alloys of nickel-titanium in tubing form may be obtained from Advanced Cardiovascular Systems, Inc, Santa Clara, Calif.

The reinforcing member 28 surrounds the core 22 from the proximal end of the drive shaft 20 to the distal end of the drive shaft 20. The reinforcing member 28 is attached to the core 22 at least at two points. The attachment is made by solder, welding, epoxy or other suitable method. With reference to FIG. 2, there is shown a first attachment point 30 at one end of the composite drive shaft 20. A second attachment is made at a second attachment point 32 at the opposite end of the drive shaft 20. The attachment of the core 22 and the reinforcing member 28 has the effect of combining the axial and torsional characteristics of the core 22 and the reinforcing member 28. The result is such that the composite drive shaft 20 behavior is improved as will be explained below with reference to FIGS. 2–4 and FIG. 10.

The elastic core 22 is generally an elongated cylinder. The reinforcing member 28 is wound helically around the core 22 in the form of a spring.

Figure 6:
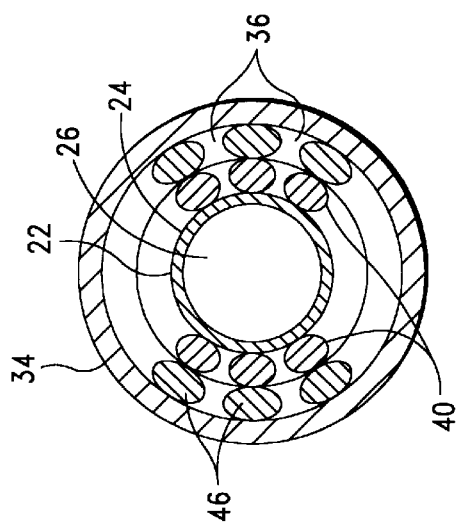
FIG. 6 is a cross section of FIG. 3 taken along line 6—6 in the direction of the arrows.

As illustrated in FIGS. 1–4, a coating 34 of polymeric material such as polyethylene, or the like is applied to the core 22 and reinforcing member 28. The coating 34 provides two functions. First, the coating 34 forms a smooth, surface for providing low surface friction for sliding in a catheter (not shown). Second, the coating 34 is applied to penetrate and impregnate the interstices 36 depicted in FIGS. 5, 6, and 7 between the reinforcement member 28 and the core 22. This penetration and impregnation binds the core 22 and member 28 more firmly together.

In a preferred embodiment shown in FIG. 2, the core 22 is shown as a tube 23 having a lumen 26 therethrough from a proximal end to a distal end. The lumen 26 acts as a passageway for introducing other instruments, e.g. a guide wire, electrical leads and the like, from the proximal end of the composite drive shaft 20 through the slipperylumen 26. The lumen 26 may also be used as a passageway for transport of atheroma material removed by the working element (not shown) on the distal end of the composite drive shaft 20 to a removing means (not shown) at the proximal end of the composite drive shaft 20.

The composite drive shaft 20 has the core 22 made from a material selected from the shape memory group of materials described above. The preferred material is an alloy of nickel-titanium having a composition of about 50% nickel and 50% titanium.

The core 22 is comprised of a thin walled tube 23 of nickel-titanium with an outside diameter in the range from 0.01 to 0.125 inches in diameter, having a wall thickness between 0.001 to 0.020 inches. The preferred dimension for this embodiment is 0.024 in. outside diameter, with a wall thickness of approximately 0.003 inch.

The core 22 is surrounded by a reinforcing helical wound spring member 40. The spring member 40 includes filament strands 44 in the form of continuous coils. The spring member 40 extends from the proximal end of the composite drive shaft 20 to the distal end of drive shaft 20. The reinforcing helical winding member 40 is a single winding of a high strength spring material such as 304 stainless steel. The preferred spring material is a flat wound wire having a 0.003 in. by 0.008 in. rectangular cross section. Spring windings having cross sections in the range of 0.001 by 0.001 to 0.010 by 0.010 inches are used to optimize other performance features.

The spring winding member 40 provides additional torsional strength to the composite drive shaft 20. The winding 40 combines with the core 22 for transmission of torsional forces as will be described below. The low bending resistance of the helical winding 40 cooperates with the high elasticity of the shape memory tube 22 to allow the composite drive shaft 20 to negotiate the sharp curves of the vascular system in a suitable manner.

The FIGS. 1–4 are shown with the reinforcing helical wound member 40 as having successive turns wound in contact. This method of winding will cause the turns of the winding 40 to assume an angle Θ relative to the axis of the core 22 as indicated in FIG. 2. The angle Θ defines the "pick" angle. The successive turns of member 40 may be spaced apart thereby decreasing the pick angle from a maximum. The pick angle of the member 40 can be selected to optimize torsional and axial stiffness characteristics of the composite drive shaft 20 for a given set of material parameters.

The core 22 provides suitably high axial strength and resistance to elongation and compression in the axial direction of the composite drive shaft 20 relative to the helical wound reinforcing member 40. The increased axial strength of the core 23 relative to the helical winding 40 provides more accurate axial positioning for the purpose of placing and moving the work performing element (not shown) than a helical winding alone.

The work performing element is positioned by pushing or pulling on the composite drive shaft 20 at the drive coupling means 38 at the proximal end of the composite drive shaft 20. During the axial movement of the drive shaft 20, the highly elastic flexural nature of the nickel-titanium core 22 and winding allows suitable bending and flexing of the composite drive shaft 20 around the tortuous passages associated with the vascular system.

The composite drive shaft 20 of this invention provides improved consistency of angular velocity and position over previous art helical wound drive shafts.

As shown in FIG. 2, a coating 34 of polymeric material such as polyethylene, or the like is applied to the core 22 and reinforcing member 40. The coating 34 provides two functions. First, the coating 34 forms a smooth, slippery surface for providing low surface friction for sliding in a catheter (not shown). Second, the coating 34 is applied to penetrate and impregnate the interstices 36 depicted in FIGS. 5, 6, and 7 between the reinforcement member 40 and the core 22. This penetration and impregnation tends to binds the core 22 and member 40 together more completely.

In the embodiment shown in FIG. 2, when rotation is initiated, the coils 44 of the reinforcing member 40 are not all in intimate contact with the nickel-titanium tube 23. Therefore the torsional stiffness coefficient for the composite drive shaft 20 is primarily determined by the properties of the core 22 and the polymeric coating 42.

As used herein, torsional stiffness coefficient ($K_t$) is defined as:
$K_t = \tau L/\theta$, where
$\tau$ = applied torque on drive cable section (in-lb)
L = length of shaft section in., and
θ = angle of wind up over length (radians)

As rotation continues the spring coils 44 begin to engage the tube 23. The spring coils 44 are constrained by contact with the outside diameter of the tube 23 from contracting. As a result the torsional stiffness coefficient $K_t$ of the composite drive shaft 20 increases to a value associated with the material of the spring member 40. When the coils 44 are fully engaged on the tube 23, the torsional stiffness of the composite drive shaft remains constant at a higher level.

This higher level continues with further rotation until the squeezing force of the spring coils 44 and the torsional stress on the tube 23 causes the material of tube 23 to enter a region of the stress-strain behavior of the selected materials known as the superelastic region. This region is characterized by lower strength and increased deformation. The lowered strength of the tube 23 material no longer permits supporting the coils 44 of the member 40 in torsion wherein Kt of the composite drive shaft 20 decreases.

Figure 10:
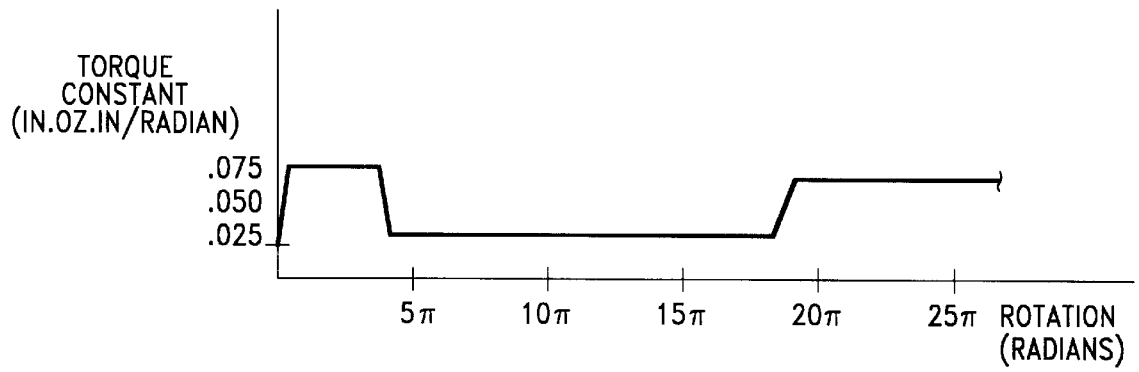
FIG. 10 is a graph of torsional stiffness coefficient vs angular displacement for the embodiment of FIG. 2.

FIG. 10 illustrates the graph of $K_t$ versus angular displacement for a 10.5 in. long sample of an embodiment of the composite drive shaft 20 depicted in FIG. 2. The embodiment has a nickel-titanium tube 23 of 0.018 inch inner diameter and 0.024 inch outer diameter. The tube 23 has a single winding 40 of a 0.004 by 0.008 inch flat wound 304 SS forming the spring coils 44. The coils 44 are attached at each end of the composite drive shaft 20 by attachment points 30 and 32 respectively. The coils 44 are impregnated with a coating of polyethylene 34.

It is the cooperation of the spring member 40, the tube 23 and the polyethylene 34 which gives increased torsional stiffness for a given degree of bending stiffness.

Another embodiment in accordance with this invention is shown in FIG. 3. The core 22 has a tubular member 23 having a lumen 26 and an outer surface 24. The core 22 has a proximal end connected to a drive coupling means 38 and a distal end connected to a working member (not shown). The reinforcing member 28 includes a first helical member 40 wound in a first winding direction around the tube 23. The reinforcing member 28 includes a second helical member 46 wound in a second winding direction on top of and opposite to the first helical member 40. The helical winding member 40 and 46 are attached to the tube 23 at first attachment points 30, 31 at one end of the composite drive shaft 20 and second attachment points 32, 33 at the opposite end of drive shaft 20.

The direction of rotation of the composite drive shaft 20 in use is such that the outside diameter of the first helical member 40 tends to expand and the outside diameter of the second helical member 46 tends to collapse. This structure gives a combined torsional stiffness coefficient for the composite drive shaft 20 greater than that of the spring members 40, 46 and core 22 alone. The torsional stiffness coefficient for the embodiment shown in FIG. 3 is essentially uniform throughout the length of the composite drive shaft 20, from the proximal end to the distal end of the shaft 20. The value of the uniform torsional stiffness coefficient for this embodiment is about 0.11 in-lb-in per radian. This structure provides a nearly constant torsional stiffness coefficient of 0.11 in-lb-in per radian from 0 to over 10π radians of angular displacement between the drive shaft 20 proximal and distal ends for a 10.5 inch length.

A drive shaft structure consisting of single or double wound springs alone for use as vascular catheter flexible drive shafts is well known in the art. The combination of such springs and a shape memory alloy core material having highly elastic flexural properties for making composite drive shafts is not known in the art and is one of the novel features in accordance with this invention.

Figure 5:
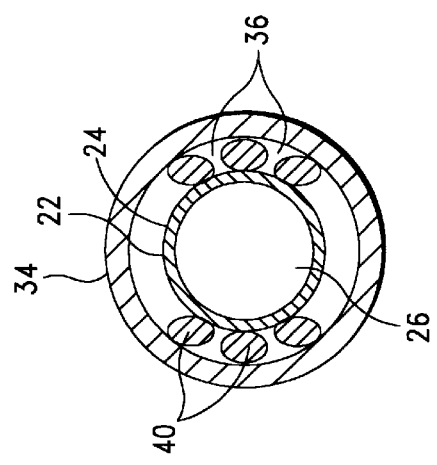
FIG. 5 is a cross section of FIG. 2 taken along line 5—5 in the direction of the arrows.

Another embodiment of the composite drive shaft 20 in accordance with this invention is depicted with reference to FIG. 2 and cross section FIG. 5. The tube 22 is formed of 0.024 inch outside diameter nickel-titanium with wall thickness 0.003 inch. The spring member 40 is a 0.003 inch by 0.008 inch flat wound quadfilar 304 stainless steel spring wound over the tube 22.

The spring member 40 and tube 23 are coated with a polyethylene sheath 34 of about 0.003 inches thickness and treated such that the polyethylene 34 penetrates the interstices 36 between the spring member 40 and the tube 23.

ALTERNATE EMBODIMENT WITH PRELOADED TORSIONAL STRAIN

With regard to FIG. 2 a preferred embodiment is described herebelow. The tube 23 and spring member 40 of the composite drive shaft 20 are first attached at a first attachment point 30 near one end of the composite drive shaft 20. The tube 23 is then twisted about π/2 radians/inch in a direction opposite to normal use. This causes the shape memory alloy tube to approach the onset of the super elastic region. Tube 23 and spring member 40 are then attached at the second attachment point 32 near the opposite end of the composite drive shaft 20. The tube 23 and the spring member 40 then are released. Tube 23 unwinds, reducing torsional strain within the tube 23, while spring member 40 winds and absorbs torsional strain until they reach a rest position.

This displacement is such that the combined tube 23 and spring member 40 have suitable preloaded, oppositely directed, torsional stress and strain built into the composite drive shaft 20 in a rest position prior to use.

The preferred range of preloaded torsional strain keeps the shape memory alloy material in the linear elastic range prior to the onset of the super elastic range. A preferred value of preloaded strain for the embodiment of FIG. 2 is about π/4 radians/inch of length of the composite drive shaft 20.

The direction of preloading is such that the spring member 40 tends to tighten down onto the tube 23 when the drive shaft 20 is rotated in a direction of normal use. This embodiment provides a torsional stiffness of about 0.075 in-lb-in per radian.

In the preloaded embodiment of FIG. 2, the preloading of the tube 23 and spring member 40 assures that the coils 44 are forced against the core in a rest condition prior to use. At the onset of rotation, the full engagement of the coils 44 with the tube 23 is already effected whereby the torsional stiffness coefficient of the composite drive shaft 20 is increased beyond that of the spring member 40 and tube 23 alone.

Rotation of the preloaded drive shaft 20 in a first direction such that the torsional force on the tube 23 initially decreases, passes through zero and approaches the super elastic region from the other direction. This causes an increase in the amount of rotation needed to move the tube 23 into the superelastic region, whereby the higher torsional stiffness coefficient of the composite drive shaft is effective over a larger angular displacement than an unloaded condition.

Figure 11:
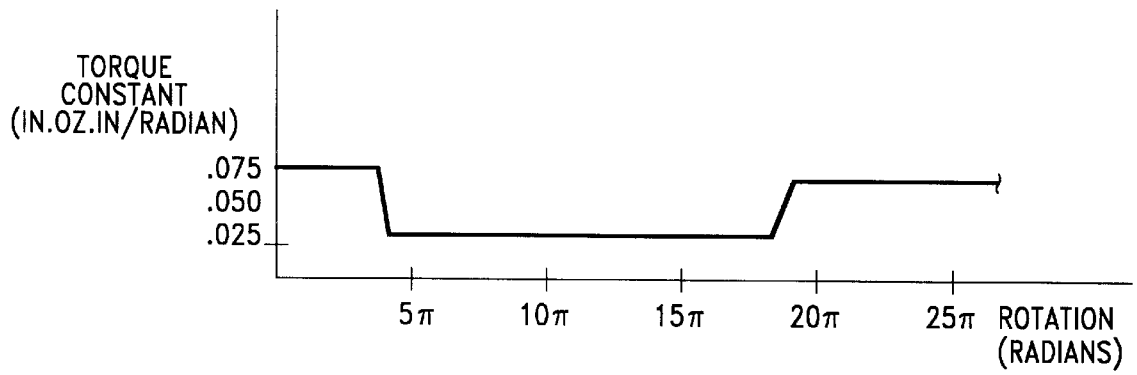
FIG. 11 is a graph of torsional stiffness coefficient vs angular displacement for an alternate embodiment of FIG. 2 with preloaded torsional strain.

The graph of Kt vs rotational displacement for the preloaded embodiment of FIG. 2 is illustrated in FIG. 11. Preloading causes the initial value of Kt at zero angular displacement to be higher than it would be without preloading.

ALTERNATE EMBODIMENT WITH OPPOSITE PRELOADED STRAIN

An alternate embodiment of the composite drive shaft 20 in accordance with this invention has the direction of preloading such that the spring member 40 tends to expand when the composite drive shaft 20 is rotated in the direction of normal use.

ALTERNATE EMBODIMENT WITH BRAIDED WINDINGS

Figure 7:
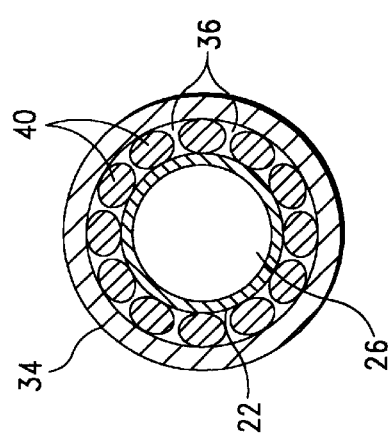
FIG. 7 is a cross section of FIG. 4 taken along line 7—7 in the direction of the arrows.

Another embodiment of the composite drive shaft 20 in accordance with this invention is illustrated in FIG. 4 and in cross section in FIG. 7. The embodiment of FIG. 4 provides equal performance in both directions of rotation. A reinforcing member comprises a first helical wound member 47 intertwined and braided with a second helical wound member 49. The first helical wound member 47 is comprised of at least one first filament element 47 wound in a first winding direction. The second helical wound member 49 is comprised of at least one second filament element 49 wound in a second, opposite winding direction. The intertwined and braided helical wound members 47, 49 are disposed between the outer surface of the core 22 and the polymeric coating 34. The helical wound members 47, 49 are attached to the core 22 near the proximal end of the composite drive shaft 20 at attachment points 30,31 and attached near the distal end of the shaft 20 at attachment points 32,33.

Figure 8:
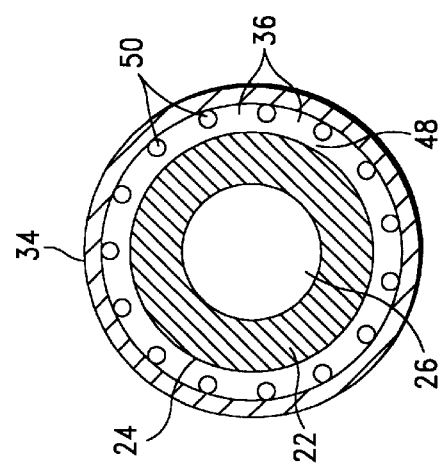
FIG. 8 is a cross section of an alternate embodiment of FIG. 2 having a spacing between the core and the inner winding.

Another embodiment in accordance with this invention is illustrated with reference to FIG. 2 and FIG. 8. This embodiment depicts a composite drive shaft 20 having the inner winding member 50 having an inside diameter larger than the outside diameter of the core 22, whereby there is a core-winding spacing 48 formed between the core 22 and the winding member strands 50. This structure is used for applications were it is desired to optimize other characteristics of the composite drive shaft 20.

Figure 9:
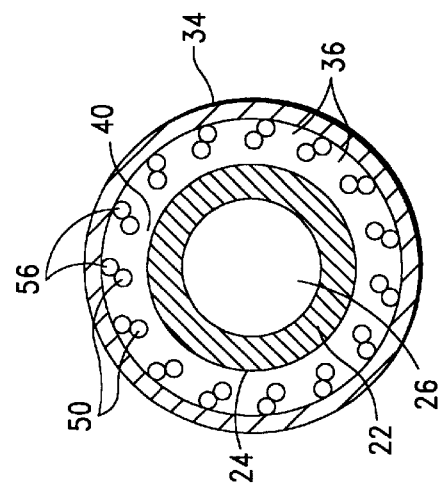
FIG. 9 is a cross section of an alternate embodiment of FIG. 3 having a spacing between the core and the inner winding.

Another embodiment is shown with reference to FIG. 3 and FIG. 9. This embodiment includes a composite drive shaft 20 having an inner winding member 50 having an inside diameter larger than the outside diameter of the core 22 and a core-winding spacing 48 formed between the core 22 and the winding member strands 50. An outer winding member 56 is wound oppositely to member 40. This structure is also used to optimize the characteristics of the composite drive shaft 20 for applications requiring bidirectional rotation.

While the foregoing detailed description has described several embodiments of the drive shaft in accordance with this invention, it is to be understood that the above description is illustrative only and not limiting of the disclosed invention. It will be appreciated that it would be possible to modify the proportions of the core and reinforcing member relative to the drive shaft length, the spring material, winding directions, number of filamentary elements, filament dimensions, open or closed windings, pick angle, core dimensions, amount and direction of preloading, core temper, composition and transition characteristics, the thickness and material used for coating and impregnation, the amount of penetration of the polymeric coating within the interstices between the windings and the core or whether impregnation is used at all. Using the principles disclosed in accordance with this invention one can predict the torsion characteristics of a drive shaft which includes or excludes various elements within the scope and spirit of this invention. Thus, the invention is to be limited only by the claims as set forth below.

What is claimed is:

1. A composite drive shaft, adapted for use with a biological catheter, comprising:

an elongated core made from a shape memory alloy, the core having a proximal and a distal end and defining a cylindrical substrate having an outer surface, the core extending from a proximal end of the drive shaft through at least a substantial portion of the drive shaft, the core being rotatable; and a reinforcing member for reinforcing the torsional strength of the composite drive shaft, the reinforcing member surrounding the core and extending from the proximal end of the core to at least the distal end of the core, the member having a first end attached to one end of the core at a first attachment point and the other end attached to the opposite end of the core at a second attachment point, the reinforcing member contracts to contact the core in response to rotation of the core to reinforce the core.

2. A composite drive shaft as set forth in claim 1, wherein the shape memory alloy core is fabricated from an alloy selected from the group of a first alloy consisting essentially of nickel-titanium; a second alloy consisting essentially of copper-zinc-aluminum; and a third alloy consisting essentially of copper-aluminum-nickel.

3. A composite drive shaft as set forth in claim 1, wherein the reinforcing member is a helical wound member wrapped around the outer surface of the core, the helical wound member comprised of at least one filamentary element.

4. A composite drive shaft as set forth in claim 1, having a polymeric coating surrounding the reinforcing member and the core.

5. A composite drive shaft as set forth in claim 1, wherein the core and the reinforcing member define interstices therebetween, and wherein a polymeric coating surrounds the reinforcing member and penetrates the interstices, whereby coupling forces between the core and the reinforcing member are substantially uniformly distributed.

6. A composite drive shaft as set forth in claim 1, wherein the reinforcing member is a double wound member comprising a first helical wound member and an oppositely wound second helical member, wherein the first helical wound member comprises at least one first filamentary element adjacent to the outer surface of the core and having a first winding direction, and the second helical wound member comprises at least one second filamentary element defining a second winding direction; and wherein the second helical wound member is disposed on the outside of the first helical wound member.

7. A composite drive shaft as set forth in claim 1, wherein the reinforcing member is comprised of a first helical wound member intertwined and braided with a second helical wound member;

wherein the first helical wound member is comprised of at least one first filamentary element wound in a first winding direction;

wherein the second helical wound member is comprised of at least one second filamentary element wound in a second, opposite winding direction; and wherein the intertwined and braided helical wound members are disposed between the outer surface of the core and the polymeric coating.

8. A composite drive shaft as set forth in claim 1, wherein the end of the core and the end of the reinforcing member opposite to the first attachment point are angularly displaced relative to the first attachment point and in relative opposition to each other prior to forming the second attachment at the second attachment point whereby the core member and reinforcing member are preloaded with opposed torsional strain.

9. A composite drive shaft as set forth in claim 8, wherein the preloaded torsional strain in the core is substantially equal to the beginning of a first superelastic region of the core in a first direction of angular displacement, whereby a torsional load placed in opposition to the preloaded strain will cause the core to traverse the full span of elastic strain from the first superelastic region to a second superelastic region in a second rotational direction opposite to the first direction of angular displacement.

10. A composite drive shaft as set forth in claim 1, wherein the core extends the full length of the drive shaft.

11. A composite drive shaft as set forth in claim 1, wherein the core extends approximately ⅔ the length of the drive shaft from the proximal end of the shaft.

12. A composite drive shaft as set forth in claim 1, wherein the composite drive shaft has a polymeric coating and defines interstices between the core and the reinforcing member, the polymeric coating penetrates interstices between the reinforcing member and the core and makes contact with the reinforcing member and the outer surface of the core to evenly distribute coupling forces between the core and the reinforcing member.

13. A composite drive shaft, adapted for use with a biological catheter, comprising:

an elongated core made of a shape memory alloy, the core having a proximal and a distal end and defining a cylindrical substrate having an outer surface, the core extending from a proximal end of the drive shaft through at least a substantial portion of the drive shaft; and a reinforcing member for reinforcing the torsional strength of the composite drive shaft having an inner surface in contact with the outer surface of the core, the reinforcing member surrounding the core and extending from the proximal end of the composite drive shaft to the distal end of the composite drive shaft, the reinforcing member having a first end attached to one end of the core at a first attachment point and the other end attached to the opposite end of the core at a second attachment point, the reinforcing member squeezes the elongated core in response to rotation of the drive shaft, whereby the drive shaft rotates and the reinforcing member contracts against the core reinforces the torsional strength of the core.

14. A composite drive shaft as set forth in claim 13, wherein the shape memory alloy core is selected from the group consisting of a first alloy constituting essentially nickel-titanium, a second alloy constituting essentially copper-zinc-aluminum and a third alloy constituting essentially copper-aluminum-nickel.

15. A composite drive shaft as set forth in claim 13, wherein the reinforcing member is a helical wound member wrapped around the outer surface of the core, the helical wound member comprised of at least one filamentary element.

16. A composite drive shaft as set forth in claim 13, having a polymeric coating surrounding the reinforcing member and the core.

17. A composite drive shaft as set forth in claim 13, having a polymeric coating surrounding and penetrating the reinforcing member, wherein the polymeric coating impregnates interstices between the core and reinforcing member, whereby coupling forces between the core and the reinforcing member are more uniformly distributed.

18. A composite drive shaft as set forth in claim 13, wherein the reinforcing member is a double wound member comprising a first helical wound member and an oppositely wound second helical member, wherein the first helical wound member is comprised of at least one first filamentary element adjacent to the outer surface of the core and having a first winding direction, and the second helical wound member is comprised of at least one second filamentary element defining a second winding direction; wherein the second helical wound member is disposed on the outside of the first helical wound member.

19. A composite drive shaft as set forth in claim 13, wherein the reinforcing member is comprised of a first helical wound member intertwined and braided with a second helical wound member;

wherein the first helical wound member is comprised of at least one first filamentary element wound in a first winding direction;

wherein the second helical wound member is comprised of at least one second filamentary element wound in a second, opposite winding direction; and wherein the intertwined and braided helical wound members are disposed on the outer surface of the core.

20. A composite drive shaft as set forth in claim 13, wherein the end of the core and the end of the reinforcing member opposite to the first attachment point are angularly displaced relative to the first attachment point and in relative opposition to each other prior to forming the second attachment at the second attachment point whereby the core member and reinforcing member are preloaded with opposed torsional strain.

21. A composite drive shaft as set forth in claim 20, wherein the preloaded torsional strain in the core is substantially equal to the beginning of a first superelastic region of the core in a first direction of angular displacement, whereby a torsional load placed in opposition to the preloaded stain will cause the core to traverse the full span of elastic strain from the first superelastic region to a second superelastic region in a second rotational direction opposite to the first direction of angular displacement.

22. A composite drive shaft as set forth in claim 13, wherein the core extends the full length of the drive shaft.

23. A composite drive shaft as set forth in claim 13, wherein the core extends approximately ⅔ the length of the drive shaft from the proximal end of the shaft.

24. A composite drive shaft as set forth in any one of claims 13 wherein the shape memory alloy core consists of essentially 50% nickel and 50% titanium.

25. A composite drive shaft for use with a biological catheter having a rotatable work element, comprising:

an elongated core, the core being made of a shape memory alloy defining a cylindrical substrate having an outer surface;

a reinforcing member coupled around the core for reinforcing the torsional strength of the composite drive shaft, the reinforcing member being impregnable by a coating; and a coating surrounding the reinforcing member and the core to facilitate composite cooperation between the reinforcing member and the core, the core and the reinforcing member define interstices therebetween which are impregnable by the coating, whereby the coating impregnates the interstices between the core and reinforcing member and binds the reinforcing member and the core to distribute coupling forces between the core and the reinforcing member.

26. A composite drive shaft as set forth in claim 25, wherein the reinforcing member is preloaded with a torsional load, when the drive shaft rotates, the reinforcing member causes the core to enter a region of stress-strain behavior known as the superelastic region.

27. A composite drive shaft as set forth in claim 25, wherein the core has a first end and second end, the core being preloaded with a torsional load to angularly displace the first end of the core with respect to the second end, when the drive shaft rotates, the angular displacement of each end changes and causes the reinforcing member to squeeze the core to cause the core to enter a region of stress-strain behavior known as the superelastic region.

28. A composite drive shaft as set forth in claim 25, wherein the reinforcing member couples to the outer surface of the cylindrical substrate.

29. A composite drive shaft as set forth in claim 25, wherein the reinforcing member has a first helical wound member and an oppositely wound second helical member, the first helical wound member has at least one first filamentary element adjacent to the outer surface of the core in a first winding direction, and the second helical wound member having at least one second filamentary element defining a second winding direction.

30. A composite drive shaft as set forth in claim 25, wherein the reinforcing member includes a first helical wound member braided with a second helical wound member, the first helical wound member has at least one first filamentary element wound in a first winding direction, the second helical wound member has at least one second filamentary element wound in a second, opposite winding direction, and each helical wound member being disposed on the outer surface of the core.

31. A composite drive shaft as set forth in claim 25, wherein the core has an outside diameter within the range of 0.01 to 0.125 inches.

32. A composite drive shaft as set forth in claim 25, wherein the cylindrical substrate is hollow having a wall with a thickness of between 0.001 to 0.020 inches.

33. A composite drive shaft as set forth in claim 25, wherein the reinforcing member is a helical winding of high strength spring material with a rectangular cross-section having dimensions within the range of 0.001 to 0.01 inches.

34. A composite drive shaft as set forth in claim 25, wherein the coating is a polyethylene sheath having a thickness of about 0.003 inches.

35. A composite drive shaft as set forth in claim 25, wherein the reinforcing member includes a helical spring having two ends, each end of the reinforcing member being attached to the core.

* * * * *